(12) United States Patent
Oppenheimer et al.

(10) Patent No.: US 12,077,505 B2
(45) Date of Patent: Sep. 3, 2024

(54) PREPARATION OF SULFONAMIDE HERBICIDE PROCESS INTERMEDIATES

(71) Applicant: Corteva Agriscience LLC, Indianapolis, IN (US)

(72) Inventors: Jossian Oppenheimer, Midland, MI (US); Matthias S. Ober, Midland, MI (US); Mark E. Ondari, Freeland, MI (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 144 days.

(21) Appl. No.: 17/296,695

(22) PCT Filed: Dec. 20, 2019

(86) PCT No.: PCT/US2019/067720
§ 371 (c)(1),
(2) Date: May 25, 2021

(87) PCT Pub. No.: WO2020/139734
PCT Pub. Date: Jul. 2, 2020

(65) Prior Publication Data
US 2022/0024873 A1 Jan. 27, 2022

Related U.S. Application Data

(60) Provisional application No. 62/785,353, filed on Dec. 27, 2018.

(51) Int. Cl.
*C07D 213/71* (2006.01)
*C07C 253/30* (2006.01)
*C07C 255/15* (2006.01)
*C07D 213/64* (2006.01)

(52) U.S. Cl.
CPC .......... *C07D 213/71* (2013.01); *C07C 253/30* (2013.01); *C07C 255/15* (2013.01); *C07D 213/64* (2013.01)

(58) Field of Classification Search
None
See application file for complete search history.

(56) References Cited

U.S. PATENT DOCUMENTS

2008/0214825 A1* 9/2008 Lehnemann ......... C07D 213/61
546/250

FOREIGN PATENT DOCUMENTS

| CN | 108558744 A | 9/2018 |
|---|---|---|
| CN | 108 707 109 A | 10/2018 |
| WO | 98/13367 A1 | 4/1998 |
| WO | 2005/063780 A1 | 7/2005 |
| WO | PCT/US2019/067720 | 3/2020 |

OTHER PUBLICATIONS

Gonzalez M. A., et al., "Process Development for the Sulfonamide Herbicide Pyroxsulam," Organic Process Research Development, Mar. 2008, vol. 12, No. 2, pp. 301-303.
International Preliminary Report on Patentability for International Application No. PCT/US2019/067720, mailed Jul. 8, 2021, 7 Pages.

* cited by examiner

*Primary Examiner* — Joseph R Kosack

(57) ABSTRACT

Improved methods for preparing chemical precursors to sulfonyl chloride III, which are important intermediates in the preparation of pyroxsulam herbicide, are provided. Also provided are compounds of Formula III, Formula VII, and IV, wherein $R^1$ is a $C_1$-$C_6$ alkyl, X is Cl or OH, Y is halogen, OH, or $OR^2$, and $R^2$ is a $C_1$-$C_6$ alkyl.

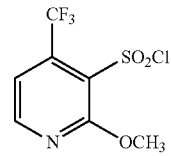

Formula III

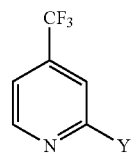

Formula IV

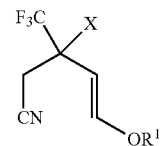

Formula VII

17 Claims, No Drawings

PREPARATION OF SULFONAMIDE HERBICIDE PROCESS INTERMEDIATES

This application claims priority to U.S. Provisional Application Ser. No. 62/785,353, filed on Dec. 27, 2018, the entire disclosure of which is hereby expressly incorporated by reference.

FIELD

This disclosure includes novel methods, novel compounds and the method of making such compounds. Such novel methods and compounds are useful intermediaries for the manufacture of other useful compounds, such as herbicides, such as pyroxsulam.

BACKGROUND

Pyroxsulam (I), a member of the triazolopyrimidine sulfonamide family, is a commercially available herbicide that offers control of many broadleaf and grass weeds in cereal crops, for example in wheat crops. The preparation of pyroxsulam has been described in for example, International PCT Application Publication WO2002036595A2 and U.S. Patent Application Publication No. 2005/0215570A1.

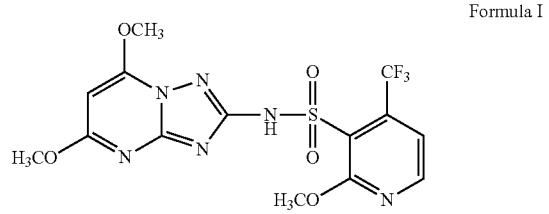 [SMILES: COc1cc(OC)n2nc(NS(=O)(=O)c3c(C(F)(F)F)ccnc3OC)nc2n1]

In conventional methods of preparation of pyroxsulam (I), the final step typically may involve coupling the amine of Formula II with the sulfonyl chloride of Formula III:

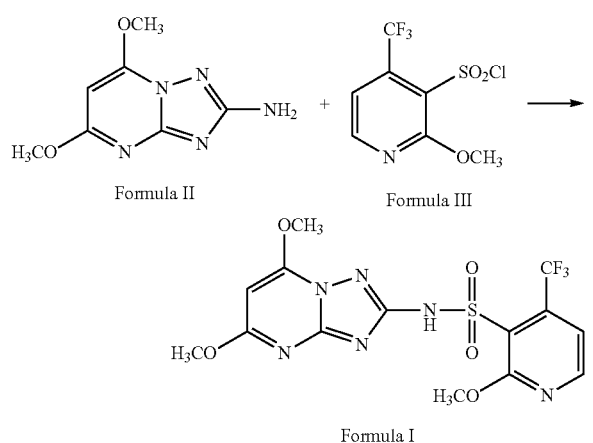

In such methods, the sulfonyl chloride III may be prepared by converting the 2-oxo-pyridine IIIa, via the 3-chloropyridine IIIb, into the 2-methoxypyridine IIIc. Sulfonyl chloride III may then be prepared by metalation/thiolation of IIIc with a mixture of lithium diisopropylamide (LDA) and elemental sulfur, followed by chloroxidation of the resulting lithiothiolate with chlorine/HCl to provide III.

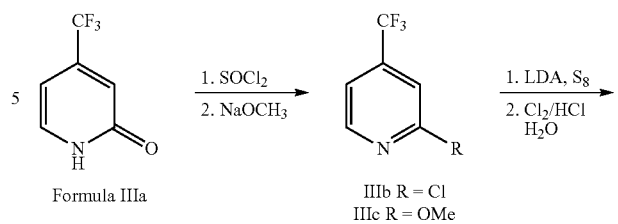

However, such conventional methods can be costly, reducing the profit, and in some cases may adversely affect the ability to use the produced pyroxsulam in some markets.

A need therefore exists to reduce the cost of the manufacture of pyroxsulam in an efficient and economic manner. Also, there is a need for the ability to make pyroxsulam in a manner that allows it to be sold in currently restricted markets.

SUMMARY

The present disclosure provides various novel compounds and their methods of preparation that allow for the novel and more cost-effective methods for preparing chemical precursors of sulfonyl chloride III, shown by Formula III below.

Such compounds can be important intermediates in the preparation of herbicides, such as pyroxsulam. Specifically, these precursors include compounds of Formula IV below, wherein Y is halogen, OH, or OCH$_3$.

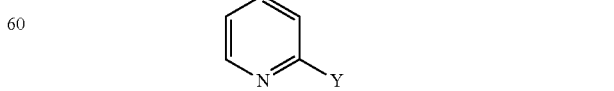

Another aspect of the present disclosure includes the novel intermediates produced by the described methods, for example, the compound of Formula VII:

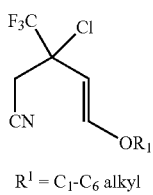

Formula VII $R^1 = C_1$-$C_6$ alkyl

In some aspects, methods comprising: combining acetonitrile, a base, and a compound of Formula V or a compound of Formula VI

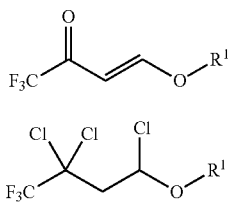

Formula V

Formula VI to form a compound of Formula VII,

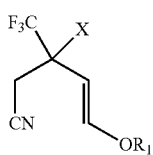

Formula VII wherein $R^1$ is a $C_1$-$C_6$ alkyl, and X is Cl or OH are provided. In some aspects, methods may also further include combining the compound of Formula VII with at least one of an acid, an alcohol, water, an alkoxide, a dehydrative halogenating reagent, or combinations thereof, to form a compound of Formula IV:

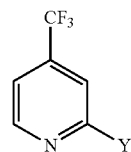

Formula IV wherein Y is a halogen, OH, or $OR^2$, and $R^2$ is a $C_1$-$C_6$ alkyl. In various aspects, the acid may be selected from the group including $H_2SO_4$, HCl, HBr, or HI, and mixtures thereof. In various aspects, the alcohol is a $C_1$-$C_6$ alcohol (e.g., methanol). In various aspects, the alkoxide is a sodium $C_1$-$C_6$ alkoxide or potassium $C_1$-$C_6$ alkoxide (e.g., sodium methoxide or potassium methoxide).

Exemplary dehydrative halogenating reagent includes $SOCl_2$, $SOBr_2$, $POCl_3$, $POBr_3$, $PCl_3$, $PBr_3$, $PCl_5$, $PBr_5$, oxalyl chloride, or mixtures thereof.

Various aspects also include methods where the combining includes the simultaneous combination of the acid and the alcohol with the compound of Formula VII to provide the compound of Formula IV wherein Y is $OR^2$, and $R^2$ is a $C_1$-$C_6$ alkyl.

Methods may also include aspects where the combining includes the simultaneous combination of the acid and water with the compound of Formula VII to provide the compound of Formula IV wherein Y is OH.

In some aspects, methods may include the sequential combination of an acid that is HCl or HBr, and then the alkoxide with the compound of Formula VII to provide the compound of Formula IV wherein Y is $OR^2$, wherein $R^2$ is a $C_1$-$C_6$ alkyl.

Some aspects include the sequential combination of the dehydrative halogenating reagent and then the alkoxide, with the compound of Formula VII to provide the compound of Formula IV wherein Y is $OR^2$, and $R^2$ is a $C_1$-$C_6$ alkyl.

In some aspects, the combining may comprise the compound of Formula IV, wherein Y is OH, and the dehydrative halogenating reagent that is thionyl chloride to provide the compound of Formula IV, wherein Y is Cl.

In various aspects, some methods may include aspects where the combining comprises the compound of Formula IV, wherein Y is halogen, and the alkoxide that is sodium methoxide or potassium methoxide to provide the compound of Formula IV, wherein Y is $OCH_3$.

Various methods also include methods further including combining the compound of Formula IV, wherein Y is $OCH_3$, with a strong base and sulfur to provide the compound of Formula IVb

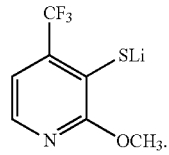

Formula IVb

Some aspects may also include methods further including the step of combining the compound of Formula IVb with $Cl_2$, HCl, and water, to provide the compound of Formula III

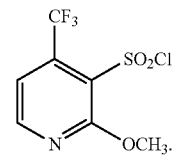

Formula III

Various compounds may include

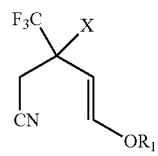

wherein $R^1$ is a $C_1$-$C_6$ alkyl, and X is Cl or OH.

DETAILED DESCRIPTION

Methods of preparing precursors of sulfonyl chloride III, an important intermediate in some preparation methods of pyroxsulam herbicides, are described. Specifically, the compounds of Formula IV, wherein Y is halogen, OH or OCH$_3$, may be prepared by the methods described herein.

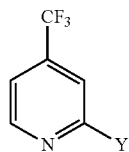

Formula IV wherein Y=halogen, OH, or OCH$_3$;

As illustrated in Schemes 1 and 2, the methods include chemical process steps that: (1) convert compounds of Formulas V or VI into the nitrile of Formula VII, and (2) convert VII into the compound of Formula IV, wherein Y is halogen, OH, or OCH$_3$, and the one or more reactants may be selected from Reactants A, B, C, D, or E, which include an acid (A), an alcohol (B), water (C), an alkoxide (D), or a dehydrative halogenating reagent (E), and combinations thereof.

Scheme 1

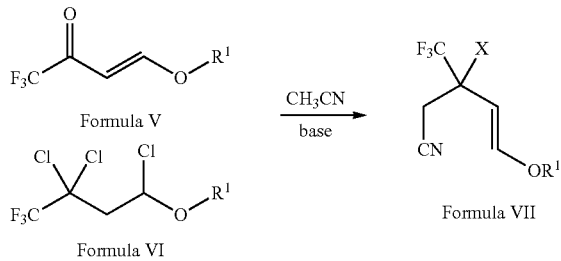

wherein R$^1$ is a C$_1$-C$_6$ alkyl and X is Cl or OH

Scheme 2

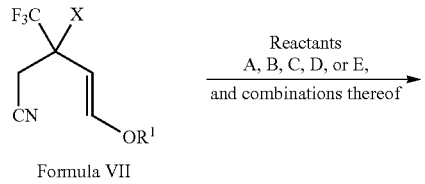

I. Definitions

As used herein, the terms "halo" or "halogen" may be understood to include one or more or F, Cl, Br, and I.

As used herein, the term "aryl," as well as derivative terms such as aryloxy, may be understood to include groups that include a monovalent aromatic carbocyclic group of from 6 to 14 carbon atoms. Aryl groups can include a single ring or multiple condensed rings. In some aspects, aryl groups include C$_6$-C$_{10}$ aryl groups. Examples of aryl groups include, but are not limited to, phenyl, biphenyl, naphthyl, tetrahydronaphthyl, phenylcyclopropyl, and indanyl. In some aspects, the aryl group can be a phenyl, indanyl or naphthyl group. The term "heteroaryl", as well as derivative terms such as "heteroaryloxy", refers to a 5-membered or 6-membered aromatic ring containing one or more heteroatoms, viz., N, O or S; these heteroaromatic rings may be fused to other aromatic systems. In some aspects, the heteroaryl group can be a pyridyl, pyrimidyl or a triazinyl group.

The aryl or heteroaryl substituents may be unsubstituted or substituted with one or more chemical moieties. Examples of suitable substituents include, for example, amino, halo, hydroxy, nitro, cyano, formyl, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, C$_1$-C$_6$ acyl, C$_1$-C$_6$ alkylthio, C$_1$-C$_6$ alkylsulfinyl, C$_1$-C$_6$ alkylsulfonyl, C$_1$-C$_{10}$ alkoxycarbonyl, C$_1$-C$_6$ carbamoyl, hydroxycarbonyl, C$_1$-C$_6$ alkyl carbonyl, aminocarbonyl, C$_1$-C$_6$ alkylaminocarbonyl, C$_1$-C$_6$ dialkylaminocarbonyl, provided that the substituents are sterically compatible and the rules of chemical bonding and strain energy are satisfied. Preferred substituents include halogen, C$_1$-C$_4$ alkyl, C$_1$-C$_{10}$ alkoxycarbonyl and C$_1$-C$_4$ haloalkyl.

II. Preparation of Nitrile VII

The first step of the method to prepare the compounds of Formula IV, wherein Y is halogen, OH, or OCH$_3$, involves the conversion of the compound of Formula V or VI into the nitrile of Formula VII, by reaction of V or VI with the lithio anion of acetonitrile, prepared from acetonitrile and a base, as shown in Scheme 3. Bases for use in this reaction step may include, but are not limited to, organolithium reagents such as n-butyllithium, sec-butyllithium, lithium diisopropylamide (LDA), and lithium or sodium hexamethyldisilazane (LHMDS or NaHMDS). Other bases such as sodium and potassium tert-butoxides (Na-tBuO and K-tBuO), tert-amyloxide can also be used. The reaction of V with lithioacetonitrile has been disclosed in U.S. Pat. No. 8,063,226, the disclosure of which is incorporated by reference in its entirety herein, whereas use of VI to make VII (X=Cl) below has not been previously disclosed.

Scheme 3

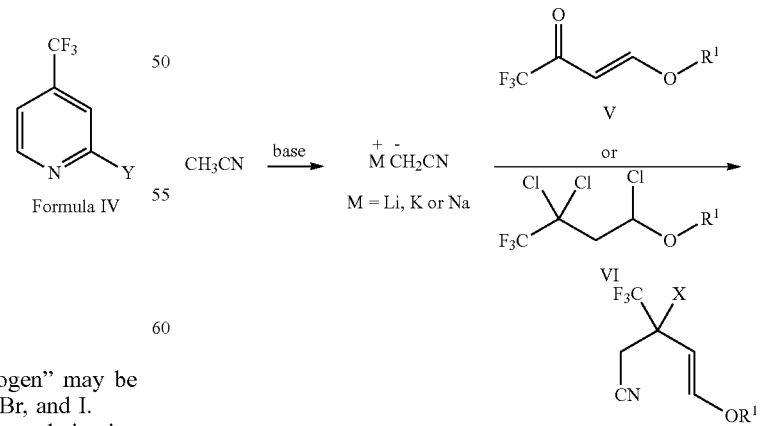

wherein R$^1$ is a C$_1$-C$_6$ alkyl and X is Cl or OH;

Compound VI can be made by the following process as described in International PCT Patent Application Publication No. WO2002053518.

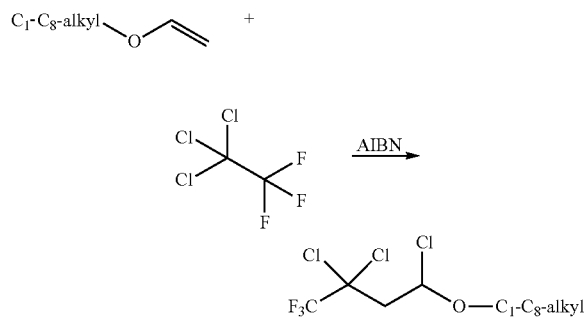

The process step to make VII can be conducted in solvents such as, but not limited to, ether solvents like THF (tetrahydrofuran), DME (1,2-dimethoxyethane), 2-methyl-THF, diethyl ether, dioxane, mixtures thereof, and mixtures of these solvents with hydrocarbon solvents such as pentane, hexane, cyclohexane, toluene, and the like. The temperature range for conducting this process step may range from about 25° C. to about −80° C., from about 0° C. to about −80° C., from about 25° C. to about −70° C., or from about 0° C. to about −70° C., and the reaction may be conducted over a time period ranging from about 1 hour to about 72 hours, from about 1 hour to about 48 hours, from about 1 hour to about 24 hours, from about 1 hour to about 12 hours, from about 1 hour to about 6 hours, or from about ½ hour to about 2 hours.

From about 1.0 to about 1.5, about 1.0 to 1.4, about 1.0 to 1.3, about 1.0 to 1.2, or from about 1.0 to 1.1 molar equivalents of the base can be used in the process to make VII.

III. Preparation of Pyridine IV

The second step of the method to prepare the compound of Formula IV involves the conversion of the compound of Formula VII, wherein $R^1$ is a $C_1$-$C_6$ alkyl and X is Cl or OH, into the compound of Formula IV by treatment with a reactant or a combination of reactants as shown in Scheme 4. The reactant or reactant combination used may preferably include a reactant that promotes cyclization of nitrile VII to pyridine IV.

Scheme 4

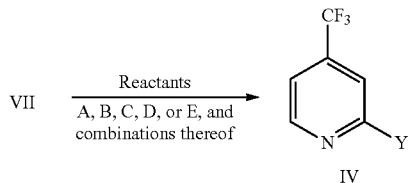

wherein Y is halogen, OH, or $OCH_3$

Table 1 below lists a number of reactants that may be used for the transformation shown in Scheme 4. Reactants A (an acid) or E (a dehydrative halogenating reagent) readily promote the cyclization of VII to IV, however, use of reactants B, C, or D alone or in combination do not readily promote cyclization of VII to IV. However, when reactants B, C, or D are used in combination with reactants A or B, either in a simultaneous manner (mixed together prior to addition to VII) or a sequential manner (added separately to VII), then cyclization of nitrile VII to pyridine IV will occur.

TABLE 1

Descriptions of Reactants A-E

| Reactant | Generic Name | Generic Reactants | Specific Reactants | Promotes Cyclization VII to IV |
|---|---|---|---|---|
| A | acid | $H_2Y$, HY | $H_2SO_4$, HCl, HBr | yes |
| B | alcohol | $C_1$-$C_6$ alcohol | MeOH, EtOH | no |
| C | water | water | water | no |
| D | alkoxide | MOR, where R = $C_1$-$C_6$ alkyl, and M = Na, K | NaOMe, KOMe | no |
| E | dehydrative halogenating reagent | $SOY_2$, $POY_3$, $PY_3$, $PY_5$ | $SOCl_2$, $SOBr_2$, $POCl_3$, $PCl_3$, oxalyl chloride | yes |

In one aspect conducted in a simultaneous manner, a mixture containing an acid and an alcohol can be combined with compound VII to provide compound IV, wherein X is Cl or OH, $R^1$ is a $C_1$-$C_6$ alkyl, and $R^2$ is $C_1$-$C_6$ alkyl. This aspect is illustrated by the following reaction:

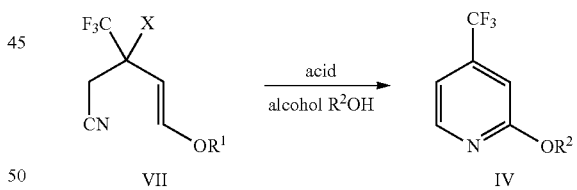

In another aspect conducted in a simultaneous manner, a mixture containing an acid and water can be combined with compound VII to provide compound IV, wherein X is Cl or OH, and $R^1$ is a $C_1$-$C_6$ alkyl. This aspect is illustrated by the following reaction:

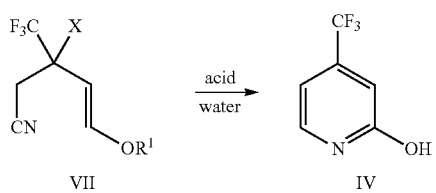

In an aspect conducted in a sequential manner, an anhydrous acid HY (Y is Cl or Br) can be combined with compound VII to provide compound IV, wherein Y is Cl or Br, which can then be combined with an alkoxide $MOR^2$ (M is Na or K) to provide compound IV wherein $R^2$ is $C_1$-$C_6$ alkyl. This aspect is illustrated by the following reactions:

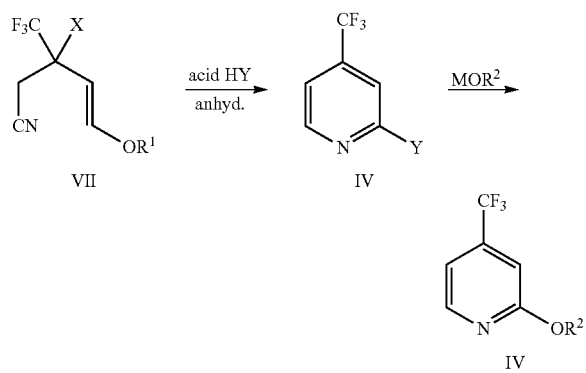

In another aspect conducted in a sequential manner, a dehydrative halogenating reagent ($SOY_2$, $POY_3$, $PY_3$, or $PY_5$) can be combined with compound VII to provide compound IV, wherein Y is Cl or Br, which can then be further combined with an alkoxide $MOR^2$ (M is Na or K) to provide compound IV wherein $R^2$ is $C_1$-$C_6$ alkyl. This aspect is illustrated by the following reactions:

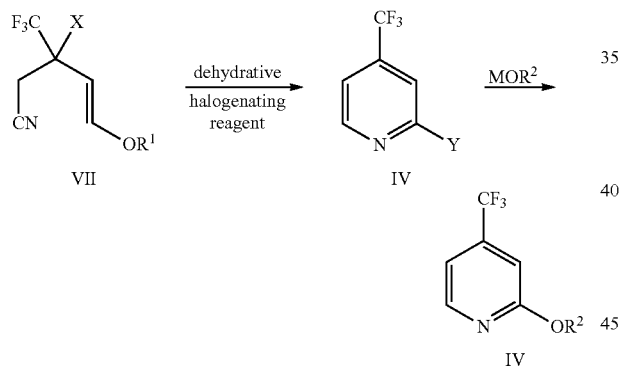

Solvents that may be suitable for use in the preparation of the substituted pyridines of Formula IV from the compounds of Formula VII include, but are not limited to, acetonitrile (ACN), N,N-dimethylformamide (DMF), dichloromethane (DCM), 1,2-dichloroethnae (DCE), tetrahydrofuran (THF), 2-methyl-THF, dioxane, cyclopentyl methyl ether, toluene, one or more xylenes, methanol, or ethanol, and mixtures thereof.

In some aspects the reactant or reactants may serve as the solvent in the preparation of the substituted pyridines of Formula IV.

The preparation of the compounds of Formula IV from the compounds of Formula VII may be conducted at a temperature of at least about 0° C., at least about 10° C., at least about 20° C., at least about 25° C., at least about 30° C., at least about 40° C., at least about 50° C., at least about 60° C., at least about 70° C., at least about 80° C., at least about 90° C., or at least about 100° C. In some aspects, the preparation of the compound of Formula IV from the compound of Formula VII may be conducted at a temperature from about 0° C. to about 50° C., from about 10° C. to about 50° C., from about 25° C. to about 50° C., from about 25° C. to about 60° C., from about 25° C. to about 70° C., from about 25° C. to about 80° C., from about 25° C. to about 90° C., from about 25° C. to about 100° C., from about 25° C. to about 125° C., or from about 25° C. to about 150° C.

IV. Preparation of 2-alkoxy-4-(trifluoromethyl)pyridine-3-sulfonyl halides IIId The compound of Formula IV can then be converted into the sulfonyl halide of Formula IIId, wherein $R^2$ is a $C_1$-$C_6$ alkyl, and Y is Cl or Br, utilizing a previous disclosed method. This conversion is shown in Scheme 5 and involves treating compound IV with a strong base and sulfur, and then treating a non-isolated lithio-sulfur intermediate with a mixture of a hydrohalide acid HY, a halogen $Y_2$, and water, wherein Y is Cl or Br, to provide the compound of Formula IIId, wherein Y is Cl or Br, and $R^2$ is a $C_1$-$C_6$ alkyl.

Scheme 5

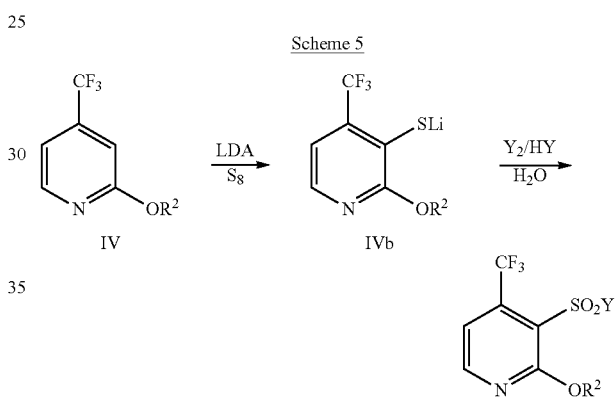

In one aspect of the preparation of the compound of Formula IIId, $Y_2$ is $Cl_2$ (chlorine; Y=Cl), the hydrohalide acid HY is HCl, and $R^2$ is $CH_3$ (e.g., the compound of Formula III).

In another aspect of the preparation of the compound of Formula IIId, a water immiscible co-solvent may be included. This co-solvent may be selected from dichloromethane, 1,2-dichloroethane, chlorobenzene, or 1,2-dichlorobenzene, or mixtures thereof.

In another aspect of the preparation of the compound of Formula IIId, a phase transfer catalyst may be included in preparation. Suitable phase transfer catalysts may include the tetraalkylammonium halides such as, for example, methyl tributylammonium chloride.

IV. Isolation/Purification

After preparation of the compounds of Formulas IV and VII by the methods described herein, the products may be isolated by employing standard isolation and purification techniques. For example, the crude product may be isolated using standard methods as described herein and purified by crystallization using a single solvent or a mixture of two or more solvents. Also, the crude product may be purified by washing it with, or stirring it in, a one, two or threecomponent solvent mixture. In one aspect, the crude product may be purified by stirring it in an aqueous alcohol solvent mixture.

The crude product may also be purified by dissolving it in one solvent to form a solution and then adding a second solvent to the solution to cause the product to crystallize out of the mixture of the two solvents.

The crude product may also be purified by distillation under vacuum.

The following examples are presented to illustrate the various aspects of the methods and compositions described herein.

EXAMPLES

Example 1a. Preparation of 2,2,4-trichloro-4-ethoxy-1,1,1-trifluorobutane

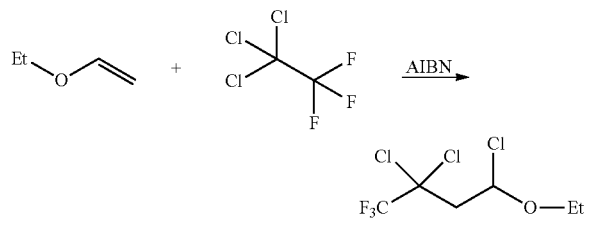

Into a 3-neck 100 mL round bottom flask was charged 1,1,1-trichloro-2,2,2-trifluoroethane (41.60 g, 220.02 mmol) and n-1-(vinyloxy)butane (9.8 g, 97.84 mmol). The mixture was heated to 45° C. followed by the addition of azobisisobutyronitrile (AIBN) (0.186 g, 1.13 mmol; immediately dissolves) The reaction mixture was heated for 10 min at 45° C. and then the temperature was heated to 50° C. The reaction mixture was heated for 4 h after which NMR of an aliquot indicated about 50% conversion. Additional AIBN (0.28 g) and 1,1,1-trichloro-2,2,2-trifluoroethane (17 g) were added and the stirring was continued at 50° C. overnight. Excess starting material was removed by distillation to give the desired product as a clear yellowish oil (17 g, 60% yield). 1H NMR (400 MHz, Chloroform-d) δ 5.97 (dd, J=7.7, 2.4 Hz, 1H), 3.95 (dt, J=9.3, 6.4 Hz, 1H), 3.56 (dt, J=9.3, 6.5 Hz, 1H), 3.12 (dd, J=15.2, 7.7 Hz, 1H), 3.01 (dd, J=15.2, 2.4 Hz, 1H), 1.71-1.57 (m, 2H), 1.50-1.32 (m, 2H), 0.94 (t, J=7.4 Hz, 3H). 13C NMR (101 MHz, Chloroform-d) δ 126.14, 123.33, 120.53, 93.42, 81.70, 81.35, 71.04, 49.98, 30.80, 19.14, 13.61.

Example 1b. Preparation of (E)-5-ethoxy-3-hydroxy-3-(trifluoromethyl)pent-4-enenitrile

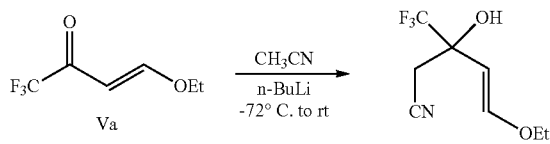

To a 125 mL 3-neck reactor equipped with a magnetic stir bar and a nitrogen inlet was loaded 50 mL 1,2-dimethoxyethane (DME), initiated stirring, and cooled to −72° C. via dry ice/isopropyl alcohol bath. To the cooled mixture was added 12.49 mL (7.98 grams) of 2.5 molar n-butyl lithium solution in hexanes (23.11 wt %) and allowed re-equilibration to −72° C. Metered in a 1.282 grams (1.631 mL) of acetonitrile, and allowed 90 minutes for total formation of anion. In a separate vial 5 g of compound Va was diluted with 10 mL of DME and the mixture metered in via syringe. The mixture was stirred for 1 h at −72° C. then the bath was removed allowing the mixture to warm up to room temperature. The mixture was quenched with of solution of $H_2SO_4$ (1.677 grams of 97 wt % sulfuric acid in 5 mL of de-ionized water). Toluene (100 mL) was then added to the mixture and stirred. The biphasic mixture was transferred to a 500 mL sep funnel and the aqueous phase was drained. The aqueous phase was re-extracted twice with 20 mL portions of toluene. The organic solution was dried over magnesium sulfate, filtered and concentrated down to a brown translucent oil. 1H NMR (400 MHz, Chloroform-d) δ 6.88 (d, J=12.7 Hz, 1H), 4.89 (d, J=12.7 Hz, 1H), 3.84 (q, J=7.0 Hz, 2H), 2.92 (d, J=16.7 Hz, 1H), 2.78 (d, J=16.6 Hz, 1H), 2.36 (s, 1H), 1.33 (t, J=7.0 Hz, 3H).

Example 1c. Preparation of (E)-3-chloro-5-ethoxy-3-(trifluoromethyl)pent-4-enenitrile

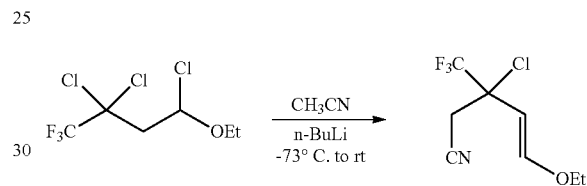

A 50 mL 3 neck round bottom flask was equipped with a magnetic stir bar, thermocouple well, nitrogen supply, a septum and an ⅛th inch compression fitting. 12 mL of anhydrous DME was added through the septum after inerting the vessel. The reactor was immersed in an IPA-dry ice bath, and the internal temperature of the reactor was allowed to reach −73° C. With a gas tight syringe, 1.17 g of a 2.5 molar n-butyl lithium solution in hexanes was injected through the septum. 0.172 grams of acetonitrile was added in a similar fashion, resulting in a dark yellow and clear solution in the reactor. An exotherm was noted upon acetonitrile addition, and a syringe pump should be used for larger volumes. The mixture was allowed to stir for 30 minutes to ensure complete anion formation. In a separate vial was added 0.172 grams of 2,2,4-trichloro-4-ethoxy-1,1,1-trifluorobutane and then it was diluted with 3 mL of anhydrous DME. The 2,2,4-trichloro-4-ethoxy-1,1,1-trifluorobutane solution was pulled into a 5 mL syringe and loaded through the ⅛ inch line by a syringe pump adding at a rate of 0.15 mL/minute. The color changed from yellow and clear to dark brown/opaque. The initial temperature was −71.5° C., and the final temperature after the 2,2,4-trichloro-4-ethoxy-1,1,1-trifluorobutane addition was −68.9° C. The mixture was stirred for 30 min at about −72° C. and then the bath was removed, allowing the mixture to warm up to 0° C. The mixture was then quenched with 1.11 grams of saturated aqueous, ammonium chloride solution by addition to the reactor at 0° C. The ammonium chloride quenched mixture was allowed to sit overnight prior to analysis. The quenched reaction mixture was taken up in toluene and washed with de-ionized water in a separatory funnel. Analysis of the crude material by NMR showed desired product was present.

Example 2a. Preparation of 2-chloro-4-(trifluoromethyl)pyridine

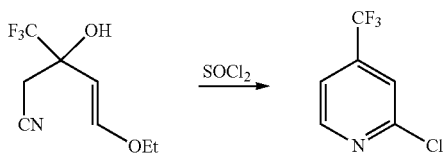 [SMILES: CCO/C=C/C(O)(CC#N)C(F)(F)F ; "SOCl2" ; FC(F)(F)c1ccnc(Cl)c1]

In a 35 mL vial with a septum cap and magnetic stir bar was added 1 gram of (E)-5-ethoxy-3-hydroxy-3-(trifluoromethyl)pent-4-enenitrile in toluene followed by 2 g of neat thionyl chloride. The mixture was placed under nitrogen. The mixture was clear and orange. The vial and its contents were heated to 50° C. for 12 hours while stirring. After 12 hours of heating, the contents of the vial were analyzed by $^1$H-NMR and $^{19}$F-NMR spectroscopy. A standard of the expected product was included in the $^{19}$F-NMR analysis for comparison. $^1$H-NMR analysis showed some impurities in the reaction mixture and $^{19}$F-NMR analysis showed conversion of the cyclization precursor to the desired 2-chloro-4-(trifluoromethyl)pyridine. Non-optimized yield of crude material: about 60%. $^1$H NMR (400 MHz, Chloroform-d) δ 8.58 (d, J=5.0 Hz, 1H), 7.57 (s, 1H), 7.48-7.41 (m, 1H).

Example 2b. Preparation of 2-methoxy-4-(trifluoromethyl)pyridine

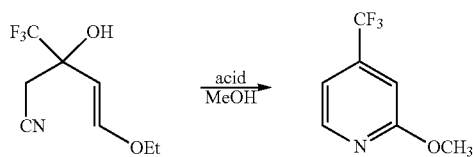 [SMILES: "MeOH" ; CCO/C=C/C(O)(CC#N)C(F)(F)F ; "acid" ; COc1cc(C(F)(F)F)ccn1]

Example 2c. Preparation of 2-hydroxy-4-(trifluoromethyl)pyridine

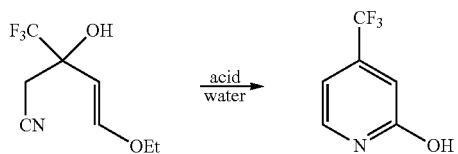 [SMILES: CCO/C=C/C(O)(CC#N)C(F)(F)F ; "water" ; "acid" ; Oc1cc(C(F)(F)F)ccn1]

The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various aspects, the terms "consisting essentially of" and "consisting of" can be used in place of "comprising" and "including" to provide for more specific aspects of the invention and are also disclosed.

What is claimed is:
1. A method comprising:
    combining acetonitrile, a base, and a compound of Formula VI

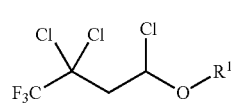

Formula VI to form a compound of Formula VII,

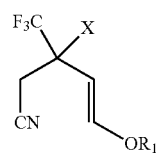

Formula VII wherein $R^1$ is a $C_1$-$C_6$ alkyl, and X is Cl or OH.

2. The method of claim 1, further comprising:
    combining the compound of Formula VII with at least one of an acid, an alcohol, water, an alkoxide, a dehydrative halogenating reagent, or combinations thereof, to form a compound of Formula IV:

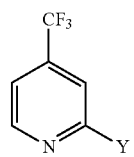

Formula IV wherein Y is a halogen, OH, or $OR^2$, and $R^2$ is a $C_1$-$C_6$ alkyl.

3. The method of claim 2, wherein the acid is selected from the group including $H_2SO_4$, HCl, HBr, or HI, and mixtures thereof.

4. The method claim 2, wherein the alcohol is a $C_1$-$C_6$ alcohol.

5. The method of claim 2, wherein the alkoxide is a sodium $C_1$-$C_6$ alkoxide or potassium $C_1$-$C_6$ alkoxide.

6. The method of claim 2, wherein the dehydrative halogenating reagent includes $SOCl_2$, $SOBr_2$, $POCl_3$, $POBr_3$, $PCl_3$, $PBr_3$, $PCl_5$, $PBr_5$, oxalyl chloride, or mixtures thereof.

7. The method of claim 2, wherein the alcohol is methanol.

8. The method of claim 2, wherein the alkoxide is sodium methoxide or potassium methoxide.

9. The method of claim 2, wherein the combining includes the simultaneous combination of the acid and the alcohol with the compound of Formula VII to provide the compound of Formula IV wherein Y is OR², and R² is a $C_1$-$C_6$ alkyl.

10. The method of claim 2, wherein the combining includes the simultaneous combination of the acid and water with the compound of Formula VII to provide the compound of Formula IV wherein Y is OH.

11. The method of claim 2, wherein the combining includes the sequential combination of an acid that is HCl or HBr, and then the alkoxide with the compound of Formula VII to provide the compound of Formula IV wherein Y is OIe, wherein $R^1$ is a $C_1$-$C_6$ alkyl.

12. The method of claim 2, wherein the combining includes the sequential combination of the dehydrative halogenating reagent and then the alkoxide, with the compound of Formula VII to provide the compound of Formula IV wherein Y is OIe, and R² is a $C_1$-$C_6$ alkyl.

13. The method of claim 2, wherein the combining comprises the compound of Formula VII, wherein X is Cl, and the dehydrative halogenating reagent that is thionyl chloride to provide the compound of Formula IV, wherein Y is Cl.

14. The method of claim 2, wherein the combining comprises the compound of Formula VII, wherein X is Cl, and the alkoxide that is sodium methoxide or potassium methoxide to provide the compound of Formula IV, wherein Y is $OCH_3$.

15. The method of claim 2, further comprising:
combining the compound of Formula IV, wherein Y is $OCH_3$, with lithium diisopropylamide and sulfur to provide the compound of Formula IVb

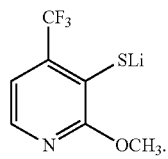

Formula IVb

16. The method of claim 15, further comprising:
combining the compound of Formula IVb with $Cl_2$, HCl, and water, to provide the compound of Formula III

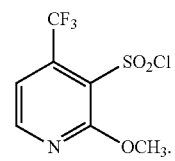

Formula III

17. A compound comprising:

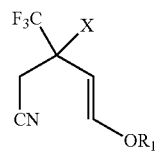

wherein $R^1$ is a $C_1$-$C_6$ alkyl, and X is Cl.

* * * * *